United States Patent [19]
Panescu et al.

[11] Patent Number: 6,129,669
[45] Date of Patent: Oct. 10, 2000

[54] SYSTEMS AND METHODS FOR ASSESSING STABILITY OF AN ABLATION ELECTRODE IN CONTACT WITH HEART TISSUE

[75] Inventors: Dorin Panescu, Sunnyvale, Calif.; Arnold J. Greenspon, Elkins Park, Pa.

[73] Assignee: Scimed Life Systems, Inc., Maple Grove, Minn.

[21] Appl. No.: 09/083,712

[22] Filed: May 22, 1998

[51] Int. Cl.[7] .................................................. A61B 5/05
[52] U.S. Cl. ............................................................ 600/424
[58] Field of Search ............................ 600/424, 372–374, 600/508, 407; 606/130; 607/116, 119, 122

[56] References Cited

U.S. PATENT DOCUMENTS

| | | | |
|---|---|---|---|
| 5,099,845 | 3/1992 | Besz et al. ............................. | 600/424 |
| 5,577,502 | 11/1996 | Darrow et al. ........................ | 128/653.1 |
| 5,598,848 | 2/1997 | Swanson et al. ...................... | 600/508 |
| 5,697,377 | 12/1997 | Wittkampf ............................. | 607/122 |
| 5,740,808 | 4/1998 | Panescu et al. . | |
| 5,868,673 | 2/1999 | Vesely ................................... | 600/407 |
| 5,876,336 | 3/1999 | Swanson et al. . | |
| 5,899,860 | 5/1999 | Pfeiffer et al. ........................ | 600/424 |
| 6,035,226 | 3/2000 | Panescu ................................ | 600/424 |

*Primary Examiner*—Marvin M. Lateef
*Assistant Examiner*—Shawna J. Shaw
*Attorney, Agent, or Firm*—Lyon & Lyon LLP

[57] ABSTRACT

Systems and methods sense stability of an ablation instrument inside a body region. The systems and methods position a tracking element in a fixed location spaced from the ablation instrument. The systems and methods generate an output, which varies according to movement of the ablation instrument relative to the tracking element over time.

4 Claims, 4 Drawing Sheets

SYSTEMS AND METHODS FOR ASSESSING STABILITY OF AN ABLATION ELECTRODE IN CONTACT WITH HEART TISSUE

FIELD OF THE INVENTION

The invention generally relates to systems and methods for guiding or locating diagnostic or therapeutic elements in interior regions of the body.

BACKGROUND OF THE INVENTION

Physicians make use of catheters today in medical procedures to gain access into interior regions of the body for diagnostic and therapeutic purposes. It is important for the physician to be able to reliably and precisely position in proximity to desired tissue locations. For example, the need for precise control over the catheter is especially critical during procedures that ablate myocardial tissue from within the heart. These procedures, called ablation therapy, are used to treat cardiac rhythm disturbances. Improved ablation outcomes are achieved when the ablation instrument is maintained in a stable position.

SUMMARY OF THE INVENTION

Systems and methods are provided for sensing stability of an ablation instrument inside a body region. The systems and methods position a tracking element in a fixed location spaced from the ablation instrument. The systems and methods generate an output, which varies according to movement of the ablation instrument relative to the tracking element over time.

In a preferred embodiment, the systems and methods visually present the output.

Other features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
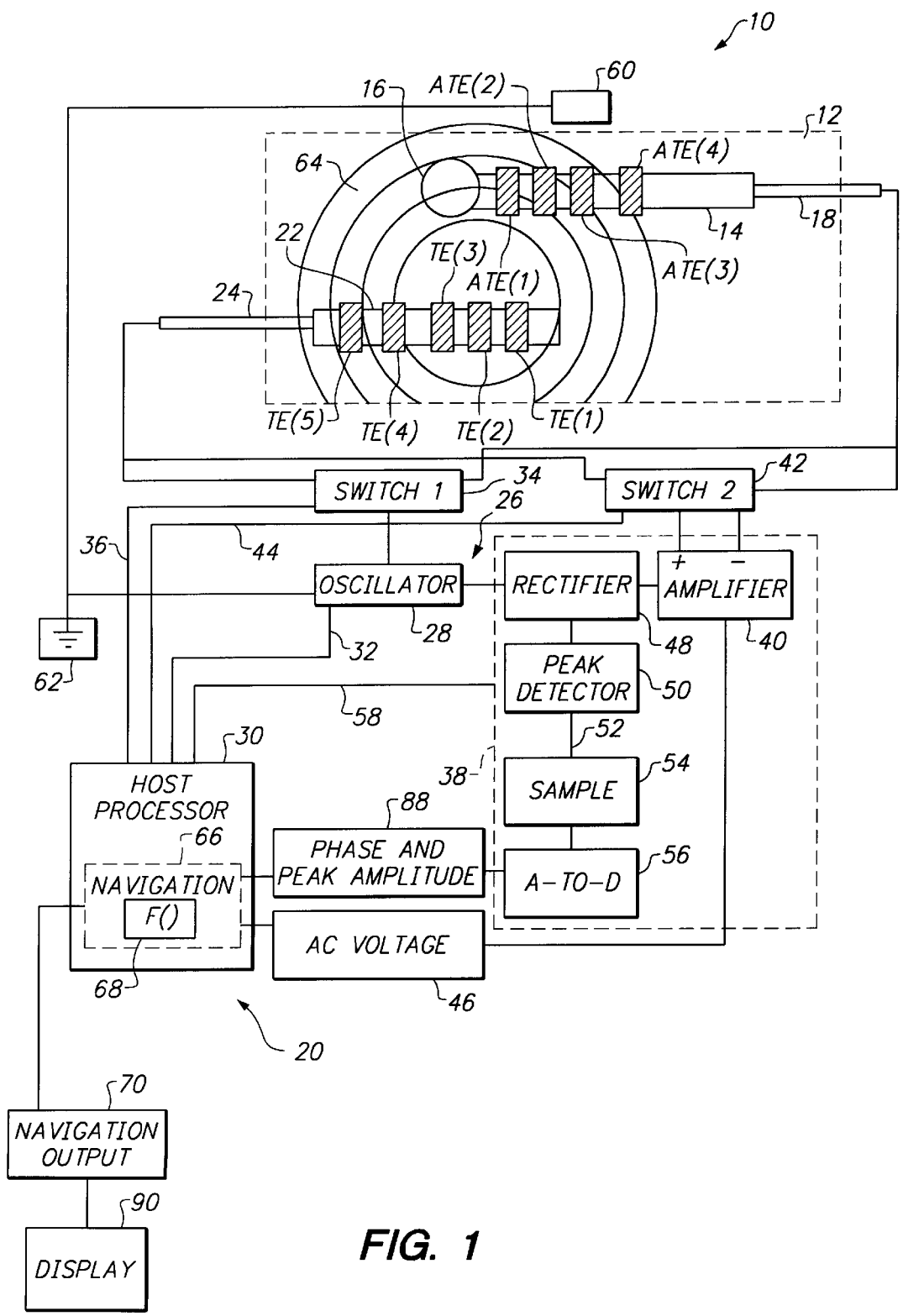
FIG. 1 is a schematic view of a stability sensing unit, which generates an output to assess the stability of an ablation electrode within a targeted body region.

FIG. 1 shows a system 10, which embodies features of the invention. The system 10 is well adapted for use inside body lumens, chambers or cavities for either diagnostic or therapeutic purposes. For this reason, the system 10 will be described in the context of its use within a living body. The system 10 particularly lends itself to catheter-based procedures, where access to the interior body region is obtained, for example, through the vascular system or alimentary canal, without complex, invasive surgical procedures.

For example, the system 10 can be used during the diagnosis and treatment of arrhythmia conditions within the heart, such as ventricular tachycardia or atrial fibrillation. The system 10 also can be used during the diagnosis or treatment of intravascular ailments, in association, for example, with angioplasty or atherectomy techniques. The system 10 also can be used during the diagnosis or treatment of ailments in the gastrointestinal tract, the prostrate, brain, gall bladder, uterus, and other regions of the body.

For purpose of illustration, FIG. 1 shows the system 10 in the context of ablating heart tissue during the diagnosis and treatment of arrhythmia conditions within the heart, such as ventricular tachycardia or atrial fibrillation.

The system 10 senses the stability, during use, of an operative element deployed within the body. For the purpose of illustration, the operative element takes the form of an ablation electrode. However, the operative element can take different forms and can be used for either therapeutic purposes, or diagnostic purposes, or both. The operative element can comprise, for example, a device for imaging body tissue, such as an ultrasound transducer or an array of ultrasound transducers, or an optic fiber element.

Alternatively, the operative element can comprise a device to deliver a drug or therapeutic material to body tissue. Still alternatively, the operative element can comprise a device, e.g., an electrode, for sensing a physiological characteristic in tissue, such as electrical activity in heart tissue, or, as in the illustrated embodiment, for transmitting energy to stimulate or ablate tissue.

I. System Components

A. The Roving Ablation Element

The system 10 includes an ablation instrument 14, which carries an ablation electrode 16. The ablation electrode 16 is intended to be mobile and capable of roving about the targeted tissue region 12 under the direction of the physician. For roving deployment in the targeted tissue region 12, the ablation electrode 16 is preferably carried at the distal end of a catheter tube 18.

In the illustrated embodiment, the ablation electrode 16 is formed from an electrically conductive metal material (e.g., copper alloy, platinum, or stainless steel). Alternatively, the ablation electrode 16 can comprise a length of wound, spiral coil made of electrically conducting material. In use, the ablation electrode 16 transmits ablation energy, e.g., in the form of radio-frequency energy, to form a lesion in myocardial tissue.

Alternatively, the ablation electrode 16 can take the form of a cannula to deliver an ablation chemical to heart tissue, or an instrument to deliver an other tissue ablating energy or substance.

B. The Stability Sensing Unit

The system 10 also includes a stability sensing unit 20, which tracks movement of the ablation electrode 16 relative to a fixed point of reference, and thus its stability, during use. The ability to sense relative motion of the electrode 16 during use allows the physician to know when the electrode 16 occupies a stable position before and during ablation, which can lead to more efficacious and consistent lesion formation.

1. The Tracking Probe

The stability sensing unit 20 includes a stationary tracking probe 22. In the illustrated embodiment, the tracking probe 22 takes the form of an elongated array of tracking electrodes NE(i), where i=1 to n, and where TE(1) denotes the most distal tracking electrode and TE(n) denotes the most proximal tracking electrode. In the illustrated embodiment, n=5.

In the illustrated embodiment, the tracking electrodes TE(i) take the form of conventional rings of electrically conductive material (e.g., copper alloy, platinum, or stainless steel), arranged in a spaced apart, segmented relationship about a sleeve of electrically insulating material. Alternatively, the tracking electrodes TE(i) can be coated upon the sleeve using conventional coating techniques or an ion beam assisted deposition (IBAD) process, or comprise spaced apart lengths of wound, spiral coils made of electrically conducting material.

The tracking probe 22 can assume different shapes. For example, the probe 22 can comprise a three dimensional array of electrodes, which assume a basket-like shape, like the CONSTELLATION® Catheter sold by EP Technologies, Inc.

In the illustrated embodiment, the tracking probe 22 is carried at the distal end of a catheter tube 24 for stationary deployment within or near the heart chamber where ablation is to occur. The tracking probe 22 may also be positioned in stationary contact with tissue or a vascular region surrounding the ablation area, or may also be positioned in stationary contact with skin on the exterior of the patient's body.

The stability sensing unit 20 also includes at least one tracking electrode ATE(j) on the movable ablation instrument 14, where j=2 to m, and where ATE(1) denotes the most distal tracking electrode on the ablation instrument 14 and ATE(m) denotes the most proximal tracking electrode on the ablation instrument 14. In the illustrated embodiment, m=4.

The tracking electrodes ATE(j) may be components added to the ablation instrument 14 strictly for navigational purposes. Alternatively, the tracking electrodes ATE(j) may comprise components used by the ablation instrument 14 for other purposes, e.g., to sense electrical activity in heart tissue or to pace heart tissue.

In the illustrated embodiment, the tracking electrodes ATE(j) on the ablation instrument 14, like tracking electrodes TE(i) on the tracking probe 22, take the form of conventional rings of electrically conductive material (e.g., copper alloy, platinum, or stainless steel), arranged in a spaced apart, segmented relationship about a sleeve of electrically insulating material. Alternatively, like the tracking electrodes TE(i), the tracking ATE(j) can be coated upon the sleeve using conventional coating techniques or an ion beam assisted deposition (IBAD) process, or comprise spaced apart lengths of wound, spiral coils made of electrically conducting material.

2. The Signal Processing Element

Still referring to FIG. 1, the stability sensing unit 22 includes a signal processing element 26. The processing element 26 includes an oscillator 28, which is coupled to a host processor 30 by a control bus 32. The host processor 30 conditions the oscillator 28 to generate an AC wave form at a predetermined amplitude and frequency.

The signal processing element 26 also includes a first electronic switch element or multiplexer 34. An address bus 36 couples the host processor 30 to the first electronic switch element 34, which is, in turn, coupled to each tracking electrode TE(i) and ATE(j). By commanding the switch element 34, the host processor 30 can distribute the AC output of the oscillator 28 in a prescribed fashion to either one or more tracking electrodes TE(i) or ATE(j).

The signal processing element 26 also includes a data acquisition module 38. The data acquisition module 38 includes a differential amplifier 40, which is coupled via a second electronic switch element or multiplexer 42 to each tracking electrode TE(i) and ATE(j). The host processor 30 conditions the second switch element 42 via a second address bus 44 to couple a selected tracking electrode TE(i) or ATE(j) to either the inverting (−) input or noninverting (+) input of the differential amplifier 40.

The output of the amplifier 40 is a differential AC voltage signal 46, which is communicated to the host processor 30 for processing, as will be described later.

In this arrangement, the signal processing element 26 can couple the oscillator 28 to any tracking electrode TE(i) or ATE(j) to transmit electrical energy. The signal processing element 26 can also sense an electrical potential at any tracking electrode TE(i) or ATE(j).

In the illustrated embodiment (see FIG. 1), the data acquisition module 38 also includes a synchronized rectifier 48 and a peak detector 50. The rectifier 48 receives the AC signal voltage output of the amplifier 40 and sense its phase relative to the phase at the output of the oscillator 28. The detector 50 determines the peak amplitude of the AC voltage signal output of the amplifier 40.

The output of the detector 50 is an analog signal 52 having a value corresponding to the peak amplitude of the AC output of the amplifier 40, and a sign (+ or −) denoting whether the AC voltage output is in phase with the oscillator 28 (+) or out of phase with the oscillator 28 (−).

The data acquisition module 38 registers this analog signal 52 in association with the electrodes then-coupled to the amplifier 40 in a sample and hold element 54. An analog to digital converter 56 converts the analog signals 52 to digital phase and peak amplitude signals 88 for processing by the host processor.

A suitable control bus 58 couples the components of the data acquisition module 36 to the host processor 30 for coordination and control functions. The host processor 30, e.g., sets the sampling rate of the sample and hold element 54, the input range of the converter 56, and the amplification of the amplifier 40.

II. System Operation

A. Generating a Position-Indicating Output

In the illustrated embodiment (FIG. 1), the host processor 30 is capable of operation in a stability sensing mode. In this mode, the host processor 30 conditions the oscillator 28 to generate an electrical alternating current (AC) waveform at a predetermined amplitude and frequency.

For use within a living body space, the selected current amplitude of the oscillator 28 output can vary between 0.05 mAmp to about 1.0 mAmp. The frequency selected can also vary from about 5 kHz to about 100 kHz. Currents substantially above about 5 mAmp and frequencies substantially below 5 kHz should be avoided when heart tissue is nearby, as they pose the danger of inducing fibrillation. The maximum current that can be used while avoiding fibrillation is a function of the frequency, as expressed in the following equation:

$$I = f \times 10 \qquad (1)$$

where I is current in μAmp (RMS), and f is frequency in kHz.

The shape of the waveform can also vary. In the illustrated and preferred embodiment, the waveform is sinusoidal. However, square wave shapes or pulses can also be used, although harmonics may be encountered if capacitive coupling is present. Furthermore, the waveform need not be continuous. The oscillator 28 may generate pulsed waveforms.

The host processor 30 commands the first switch element 34 to transmit the electrical waveform supplied by the oscillator 28 through a selected one or more tracking electrodes TE(i) on the tracking probe 22. An indifferent electrode 60, e.g., carried as a patch on the exterior of the patient, comprises the voltage return, which is, in turn, coupled to an electrical reference 62. In the illustrated embodiment, the electrical reference 62 is isolated or patient ground, although other references can be used. Alternatively, a tracking electrode TE(i) not serving to transmit the electrical waveform can serve as the voltage return.

The transmission of electrical energy from the transmitting tracking electrode TE(i) to the indifferent electrode 60 establishes a voltage field 64. The voltage field 64 extends from the transmitting electrode into the targeted tissue region 12. The field 64 surrounds the ablation instrument 14 present within the region 12.

The host processor 30 conditions the data acquisition module 38 to sense local voltages within the field 64 between the transmitting tracking electrode or electrodes and one of the tracking electrodes ATE(j) on the ablation instrument 14. For example, in a preferred embodiment, the data acquisition module 38 senses voltage amplitudes at the transmitting tracking electrode TE(i) and the other tracking electrode ATE(j).

The data acquisition module 38 can also be conditioned to sense other electrical characteristics in the field 64 in addition to voltage amplitudes. For example, using the rectifier 48 and detector 50, the data acquisition module 38 can acquire spacial variations in phase or spacial variations in waveform within the field. The data acquisition module 38 can also acquire variations in impedances between the transmitting tracking electrode TE(i) and the other tracking electrode ATE(j).

The host processor 30 inputs the electrical field data signals 46 and 88 into a prescribed position sensing algorithm 66, which resides on the host processor 30. The algorithm 66 includes prescribed functions 68, which processes sensed electrical field data based upon empirically derived mathematical coefficients and weighing factors to generate a position-indicating or navigation output 70. The navigation output 70 indicates the position of the tracking electrode ATE(j) on the movable ablation instrument 14 relative to the stationary transmitting tracking electrode TE(i) on the tracking probe 22. The navigation output 70 thereby provides an instantaneous indication of the position of the ablation instrument 14. Over time, the navigation output 70 also indicates change in the position of the ablation instrument 14 within the heart chamber 12, and, therefore, its stability.

In the illustrated embodiment (FIG. 1), the stability sensing unit 20 includes a display device 90 (e.g., a CRT, LED display, or a printer). As will be described in greater detail later, the device 90 presents changes in the navigation output 70 over time in a visual or audio format useful to the physician for ascertaining the stability of the ablation electrode 16.

Figure 2:
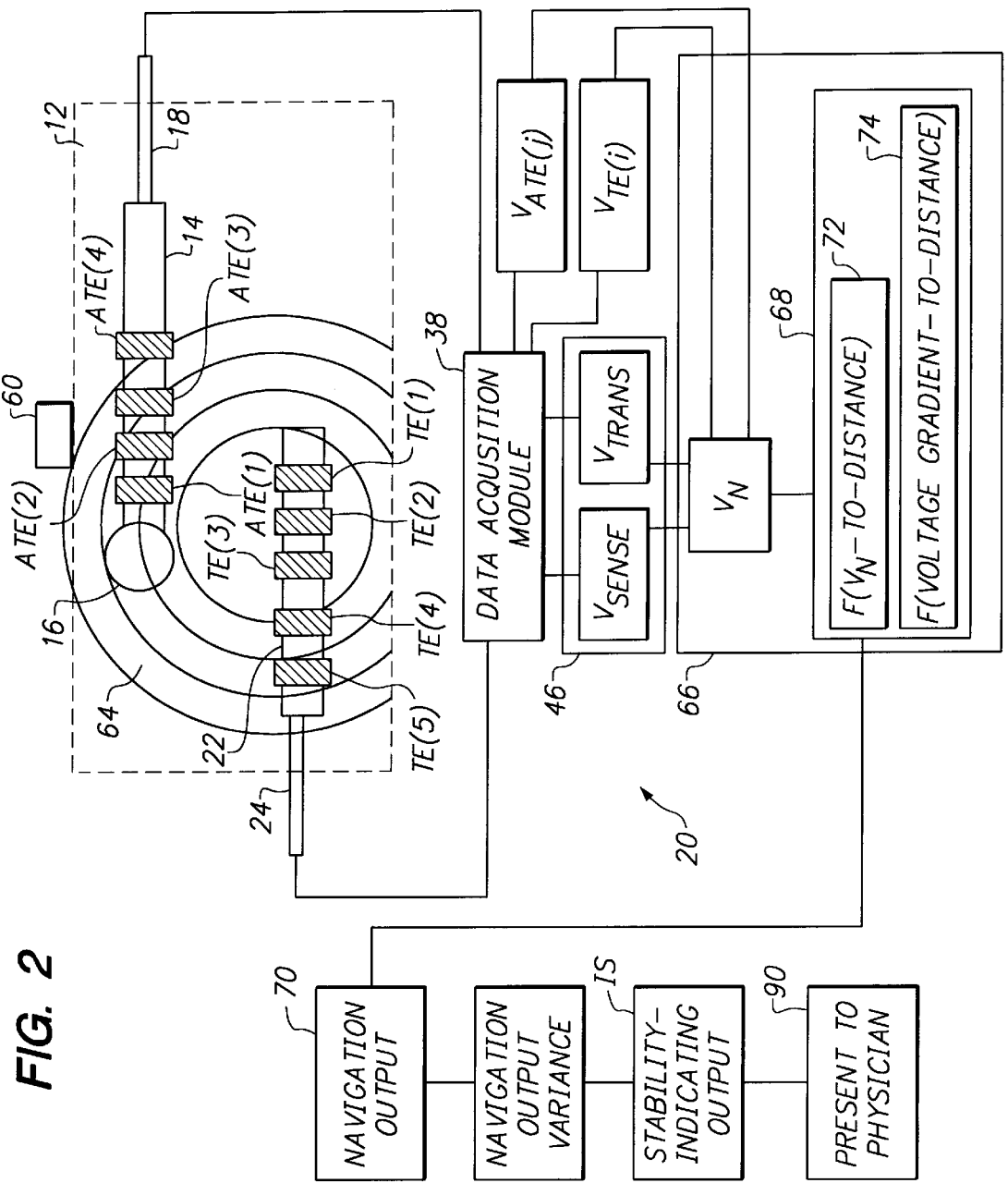
FIG. 2 is a schematic view of the stability sensing functions of the navigation unit shown in FIG. 1.

The technique for acquiring and processing sensed electrical field data can vary. In a preferred embodiment (see FIG. 2), the algorithm 66 processes the local amplitude values 46 of the voltage field sensed by the tracking electrode ATE(j) on the ablation instrument 14. The local voltage amplitude values vary based upon a determinable voltage-to-distance function 72, as the distance between the tracking electrode ATE(j) and the transmitting tracking electrode TE(i) on the probe 22 varies.

To acquire voltage amplitude data, the data acquisition module 38 conditions the tracking electrode TE(i) that is currently transmitting the electrical field (which will also be called the "transmitting electrode") to itself sense a local voltage amplitude, or $V_{TE(i)}$. The data acquisition module 38 also conditions the tracking electrode ATE(j) on the ablation instrument 14 to sense a local voltage amplitude, or $V_{ATE(j)}$, at the same time $V_{TE(i)}$ is sensed by the tracking electrode TE(i). $V_{ATE(j)}$ is acquired in association with each $V_{TE(i)}$.

Based upon this input, the algorithm 66 derives a normalized detected voltage value, designated $V_{N(i,j)}$, for each acquired $V_{TE(i)}$ and $V_{ATE(j)}$ data set, as follows:

$$V_{N(i,j)} = \frac{V_{TE(i)}}{V_{ATE(j)}} \qquad (2)$$

More universally expressed, the normalized detected voltage value $V_N$ is derived by dividing the local voltage amplitude sensed by the transmitting tracking electrode (universally designated $V_{TRANS}$) into the local voltage amplitude sensed by the other non-transmitting, sense-only tracking electrode (universally designated $V_{SENSE}$), or:

$$V_N = \frac{V_{SENSE}}{V_{TRANS}} \qquad (3)$$

Applying this more universal expression, the stability sensing unit 20 can obtain electrical field data by coupling the oscillator 28 to any tracking electrode ATE(j) on the ablation instrument 14 to generate the electric field between it and the indifferent electrode 60. Alternatively, another tracking electrode ATE(j) on the ablation instrument 14 not serving to transmit the energy field, or one of the other tracking electrodes TE(i) on the tracking probe 22, can serve as the voltage return. In this alternative implementation, the data acquisition module 38 individually conditions a selected tracking electrode TE(i) on the probe 22 (or, in sequence, several tracking electrodes on the probe 22) to sense a local voltage amplitude $V_{TE(i)}$, which corresponds to the quantity $V_{SENSE}$ in Equation (3). The data acquisition module 38 also conditions the transmitting tracking electrode ATE(j) on the ablation instrument 14 to itself sense a local voltage amplitude $V_{ATE(j)}$ at the same time $V_{TE(i)}$ is sensed by each tracking electrode TE(i) on the probe 22, which corresponds to the quantity $V_{TRANS}$ in Equation (3).

As the foregoing discussion demonstrates, the navigation output 70 can be generated either by sensing using one or more of the tracking electrodes on the ablation instrument 14 or by sensing using one or more of the tracking electrodes on the probe 22.

In this arrangement, the algorithm 66 derives a normalized detected voltage value $V_{N(i,j)}$ for each acquired $V_{ATE(j)}$ and $V_{TE(i)}$ data set, as follows:

$$V_{N(i,j)} = \frac{V_{TE(i)}}{V_{ATE(j)}} \qquad (4)$$

The algorithm 66 (see FIG. 2) incorporates a voltage-to-distance function 72, according to which the normalized voltage $V_N$ (i.e., $V_{SENSE}/V_{TRANS}$) decays to zero as the distance between the sensing electrode ($E_S$) and the transmitting electrode ($E_T$) [or $d(E_S-E_T)$] increases.

The voltage-to-distance function 72 relating normalized voltage $V_N$ to the navigation output $d(E_S-E_T)$, can be mathematically expressed, e.g., as follows:

$$V_n = f(\lambda_1, \lambda_2, \ldots, \lambda_x d(E_S-E_T)) \quad (5)$$

In Equation (5), f is a continuous, monotonically decreasing function. The quantities $\lambda_{1\text{-}to\text{-}x}$ are coefficients and weighing factors, which can be determined and assigned values experimentally, e.g., by in vitro or in vivo testing or by finite element analysis.

Because the function f is continuous and monotone, the navigation output $d(E_S-E_T)$ can itself be expressed as a unique inverse function $f^{-1}$ of the normalized voltage $V_N$, as well as inverse coefficients and weighing factors $\lambda_{1\text{-}to\text{-}n}$, e.g., as follows:

$$d(E_S-E_T) = f^{-1}(\lambda_1, \lambda_2, \ldots, \lambda_y, V_N) \quad (6)$$

The inverse function $f^{-1}$ of Equation (6) can be approximated using various numeric methods. For example, approximation by Taylor series could be used.

Applying the inverse function $f^{-1}$ based upon sensed electrical conditions in the field, the navigation algorithm 66 generates the navigation output 70, which expresses $d(E_S-E_T)$.

In addition to the empiric voltage-to-distance function 72, the algorithm 66 can apply other empiric functions 74 (see FIG. 2) which include coefficients and weighing factors expressing relationships between distance and the spacial distribution of voltage gradients sensed in the field 64. For example, the algorithm 66 can include in the generation of the navigation output 70 the application of coefficients and weighing factors relating changes in position to variations in phase sensed in the field, as disclosed in patent application Ser. No. 08/320,301, filed Oct. 11, 1994, (now abandoned) and entitled "Systems and Methods for Guiding Movable Electrode Elements Within Multiple Electrode Structures." As another example, the algorithm 66 can also include in the generation of the navigation output 70 the application of coefficients and weighing factors relating changes in position to variations in waveform sensed in the field, as disclosed in copending patent application Ser. No. 08/745, 795, filed Nov. 8, 1996, and entitled "Systems and Methods for Locating and Guiding Operating Elements Within Interior Body Regions." Further discussion of these alternative functions 74 will appear later.

B. Generating a Stability Output

Figure 3:
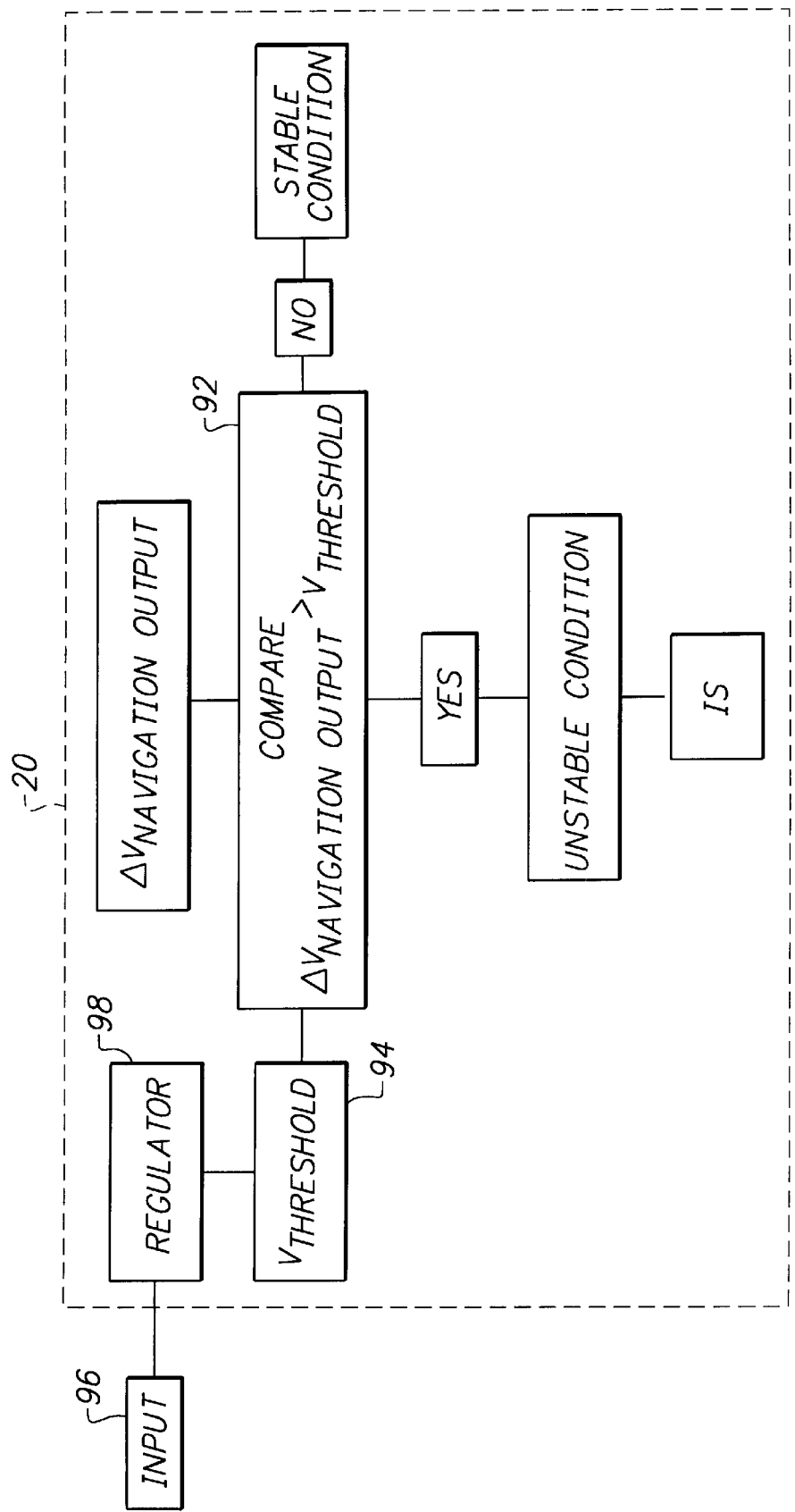
FIG. 3 is a schematic view of the stability sensing algorithm, which provides an instability output indicating that the ablation electrode is not in stable contact with heart tissue.

The coefficients $\lambda_{1\text{-}tp\text{-}y}$ convert the normalized voltage amplitude to periodically express the position-indication output 70 as a voltage value ($V_{NAVIGATION\ OUTPUT}$). The stability sensing unit 20 derives a change in the navigation output 70 over time ($\Delta V_{NAVIGATION\ OUTPUT}$), expressed as a voltage value, over successive time periods. Referring to FIG. 3, the stability sensing unit 20 includes a comparator 92, which receives as input the voltage value $\Delta V_{NAVIGATION\ OUTPUT}$ for each time period. The comparator also receives as input a set line voltage 94, which constitutes a predetermined nominal voltage threshold value $V_{THRESH}$. The comparator 92 compares the magnitude of voltage value $\Delta V_{NAVIGATION\ OUTPUT}$ to the magnitude of $V_{THRESH}$.

The predetermined nominal voltage threshold value $V_{THRESH}$ is selected to establish a nominal voltage value variance that is attributable to normal background electrical noise or incidental movement of the ablation instrument 14 due, e.g., to normal heart activity. The threshold voltage value $V_{THRESH}$ serves to differentiate between a "stable condition" for the ablation instrument 14 (i.e., when $\Delta V_{NAVIGATION\ OUTPUT}$ is equal to or less than the normal voltage variance value) and an "unstable condition" for the ablation instrument 14 (i.e., when $\Delta V_{NAVIGATION\ OUTPUT}$ greater than the nominal voltage variance value).

If $\Delta V_{NAVIGATION\ OUTPUT}$ is greater than $V_{THRESH}$, the comparator generates an instability-indicating output, also designed IS for the ablation instrument 14. The instability-indicated output IS notifies the physician that the ablation instrument 14 is not stable enough to generate an efficacious lesion.

When $\Delta V_{NAVIGATION\ OUTPUT}$ is equal to or less than $V_{THRESH}$, the comparator generates no output. The absence of an instability-indicating output IS notifies the physician that the requisite stability exists for efficacious lesion formation.

Aided by the instability=indicating output IS, the physician can manipulate the ablation instrument until no instability-indicating output is generated. At that time, the physician can apply ablation energy to the ablation electrode 16 to create a lesion in the adjacent heart tissue.

The magnitude selected for the threshold value $V_{THRESH}$ sets the spacial criteria for a "stable condition" and an "unstable condition," given the physical characteristics of the tracking electrodes TE(i) and ATE(j). The physical characteristics include the diameter and shape of the electrodes, as well as the electrical conductivity of the material or materials from which the electrodes are made and the electrical properties of the conductive medium existing between the probe 22 and the ablation instrument 14.

The value of $V_{THRESH}$ can be set at a desired fixed voltage value representing a nominal threshold distance. In the illustrated and preferred embodiment (see FIG. 3), the navigation unit 20 includes an input 96 by which the physician can designate a value for the nominal voltage variance. The navigation unit 20 also includes a voltage regulator 98, which sets the voltage line input 94 to the normalized voltage variance value ($V_{THRESH}$), to thereby achieve the spacial sensitivity established by the physician or the instability-indicating output IS.

C. Displaying the Stability Output

As before described, the system 10 includes an output display device 90, which presents changes in the navigation output 70 over time in a format useful to the physician for ascertaining the stability of the ablation electrode 16. The format display of the device 90 may present the navigation output 70 in various ways.

Figure 4:
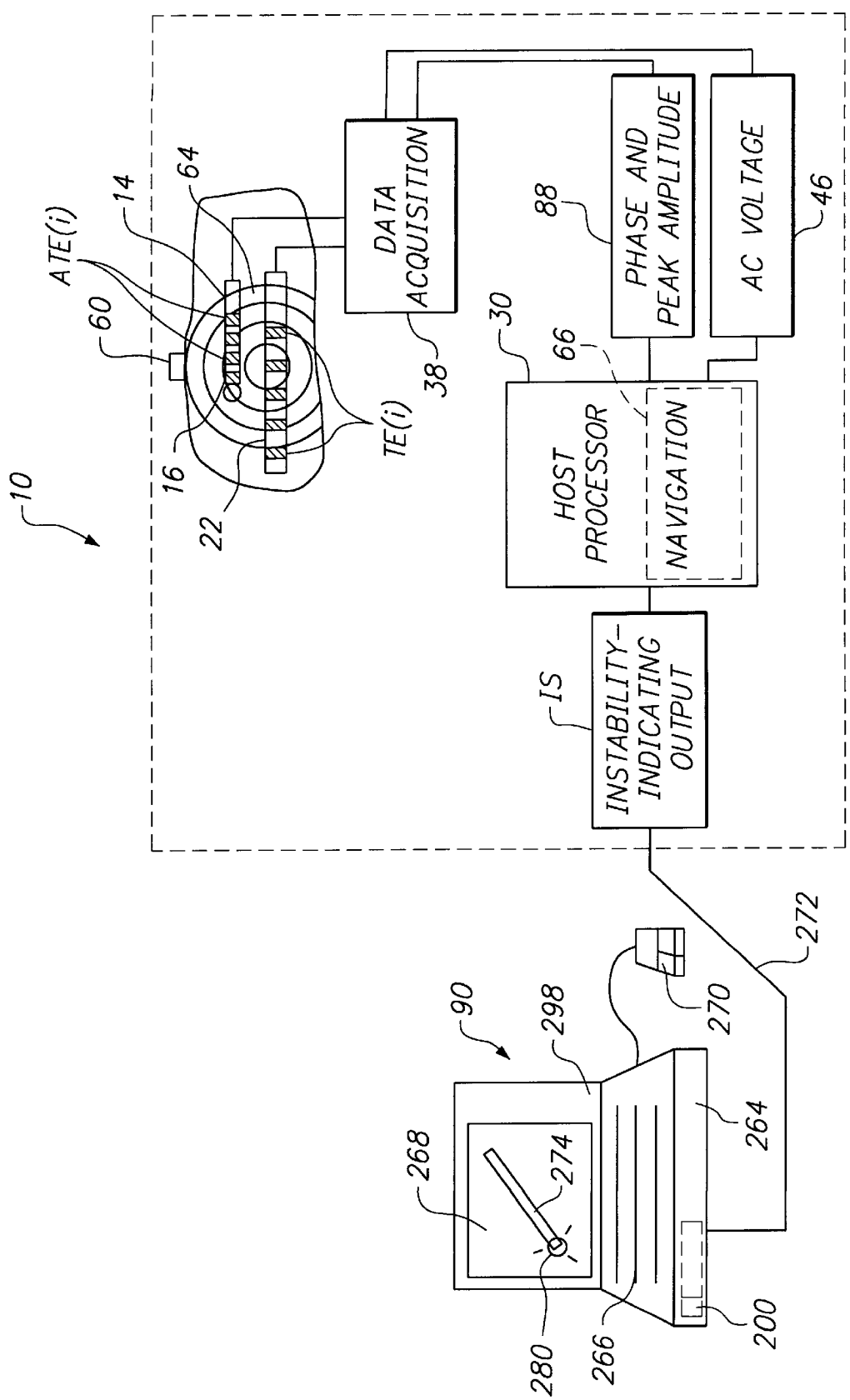
FIG. 4 is a schematic view of a graphical user interface for displaying the instability output.

In the embodiment shown in FIG. 4, the output display device 90 comprises a Graphical User Interface (GUI) 298. In the illustrated embodiment, the GUI 298 is implemented by a graphical control program 200 resident in an external microprocessor based computer control, such as laptop computer 264 having a keyboard 266, a display screen 268, and mouse 270. The laptop computer 264 is coupled to the host processor 30 via a communication port 272, such as RS 232 or an Ethernet™ connection.

The host processor 30 conditions the GUI graphical control program 200 to generate on the display screen 268 an idealized graphical image 274, which models the geometry of the particular roving ablation element 14 deployed in the body region. The image 274 of the ablation element 14 can appear, e.g., as a modeled wire-frame image, with the ablation electrode 16 appearing as a node 280.

The GUI control program 200 initializes the node 280 on the model image 274 at a designated color or shade. The initialized color or shade for the node 280 constitutes a default visual signal to the physician, that the ablation electrode 16 is in a stable condition.

The generation of an instability-indicating output IS by the navigation algorithm 66 is transmitted to the control program 200. The control program 200 switches "ON" the node 280, by changing the designated color or shade. The node 280, when switched "ON," displays a different color or shade, e.g., red color, or a graphically "blurred" appearance, to visually signal the physician that the ablation electrode 16 is in an unstable condition. The physician can then reposition the ablation electrode 16 until the instability-indicating output IS is no longer generated, and the GUI 298 returns the node 280 to its normal default condition.

The foregoing GUI 298 and implementing control programs can be implemented using the MS WINDOWS™ application and the standard controls provided by the WINDOWS™ Development Kit, along with conventional graphics software disclosed in public literature. Other details of the GUI 298 can be found in patent application Ser. No. 08/938,721, filed Sep. 26, 1997, (now abandoned) and entitled "Systems and Methods for Generating Images of Structures Deployed Within Interior Body Regions.".

Various features of the invention are set forth in the following claims.

We claim:

1. A system for sensing stability of an operative instrument inside a body region, comprising:

a stationary tracking element spaced from the operative instrument, a signal processing element coupled to the stationary tracking element and the operative instrument to generate an output voltage value indicative of movement of the operative instrument relative to the stationary tracking element over time, and a comparator that compares the output voltage value with a threshold voltage value and generates an instability-indicated output based on the comparison, wherein the threshold voltage value differentiates between a stable condition and an unstable condition.

2. A system according to claim 1, further including a display device for presenting the instability-indicated output.

3. A method of sensing stability of an operative instrument inside a body region, comprising:

positioning a tracking element in a fixed location spaced from the operative instrument, generating an output voltage indicative of movement of the operative instrument relative to the stationary tracking element over time, and comparing the output voltage value with a threshold voltage value and generating an instability-indicated output based on the comparison, wherein the threshold voltage value differentiates between a stable condition and an unstable condition.

4. A method according to claim 3, further including visually presenting the instability-indicated output.

* * * * *